(12) United States Patent
Tohidi et al.

(10) Patent No.: US 9,310,350 B2
(45) Date of Patent: Apr. 12, 2016

(54) EARLY WARNING SYSTEM FOR HYDRATE OR CLATHRATE MATERIALS

(75) Inventors: Bahman Tohidi, Edinburgh (GB); Jinhai Yang, Edinburgh (GB); Antonin Chapoy, Bo'ness (GB); Saeid Mazloum, Edinburgh (GB)

(73) Assignee: HERIOT-WATT UNIVERSITY, Edinburgh (GB)

( * ) Notice: Subject to any disclaimer, the term of this patent is extended or adjusted under 35 U.S.C. 154(b) by 84 days.

(21) Appl. No.: 14/118,159

(22) PCT Filed: May 16, 2012

(86) PCT No.: PCT/GB2012/000439
§ 371 (c)(1),
(2), (4) Date: Mar. 25, 2014

(87) PCT Pub. No.: WO2012/156669
PCT Pub. Date: Nov. 22, 2012

(65) Prior Publication Data
US 2014/0220692 A1    Aug. 7, 2014

(30) Foreign Application Priority Data
May 17, 2011   (GB) .................................. 1108224.5

(51) Int. Cl.
*G01N 33/28* (2006.01)
*G01N 33/26* (2006.01)
*G01N 33/22* (2006.01)

(52) U.S. Cl.
CPC .......... *G01N 33/2847* (2013.01); *G01N 33/225* (2013.01); *G01N 33/2829* (2013.01)

(58) Field of Classification Search
CPC .......... G01N 33/2847; G01N 33/2829; G01N 33/28; G01N 33/26; G01N 33/00
USPC .................................. 436/40, 39; 422/83, 50
See application file for complete search history.

(56) References Cited

U.S. PATENT DOCUMENTS

2007/0276169 A1    11/2007   Tohidi

FOREIGN PATENT DOCUMENTS

| WO | WO2006054076 A1 | 5/2006 | |
| WO | WO 2010/004289 | * 1/2010 | ........... G01N 29/024 |

OTHER PUBLICATIONS

Anderson, Ross et al, Phase Relations and Binary Clathrate Hydrate Formation in the System H2-THF-H2O, 2007, Langmuir, 23, 3440-3444.*
European Patent Office, International Application No. PCT/GB2012/000439 International Search Report and Written Opinion dated Jul. 25, 2012, pp. 1-10.

(Continued)

*Primary Examiner* — Christine T Mui
(74) *Attorney, Agent, or Firm* — Christopher J. Knors; Moore & Van Allen PLLC (57) ABSTRACT

A method of detecting hydrate formation includes monitoring a gas phase of interest. The gas phase is a mixture of gases comprising at least one hydrate forming gas. The monitoring includes determining the concentration of at least one component of the mixture of gases, or determining a ratio of concentration between two components of the mixture, at least one of which is the hydrate forming gas. When a change in the determined concentration or in the determined ratio of concentration is detected, relative to an earlier determination or relative to a pre-established base level concentration or base level range of concentration then formation of a hydrate is indicated. Apparatus for carrying out the method and methods for estimating the location of hydrate formation in a pipeline are also described.

16 Claims, 5 Drawing Sheets

(56) References Cited

OTHER PUBLICATIONS

B. Tohidi et al., "Developing a Hydrate-Monitoring System", (Conference Info: SPE Projects Facilities & Contruction 4), vol. 4, No. 1, Mar. 1, 2009, pp. 1-6.

Tsutomu Uchida et al., "Kinetics and Stability of CH4-COx Mixed Gas Hydrates during Formation and Long-Term Storage", Chemphyschem, vol. 6, No. 4, Apr. 15, 2005, pp. 646-654.

Tsutomu Uchida et al., "Two-Step Formation of Methane-Propane Mixed Gas Hydrates in a Batch-Type Reactor", AICHE Journal, vol. 50, No. 2, Feb. 10, 2004, pp. 518-523.

Z.M. Zain, et al., "Hydrate Monitoring and Warning System: A New Approach for Reducing Gas Hydrate Risks", Society of Petroleum Engineers Inc., 14th Europec Biennial Conference, Jun. 13, 2005, pp. 1-8.

\* cited by examiner

EARLY WARNING SYSTEM FOR HYDRATE OR CLATHRATE MATERIALS

CROSS-REFERENCE TO RELATED APPLICATIONS

This application is filed under the provisions of 35 U.S.C. §371 and claims the benefit of International Patent Application No. PCT/GB2012/000439, filed on Sep. 16, 2012, which claims the benefit of Patent Application No. 1108224.5, filed in Great Britain on Sep. 17, 2011; all of which are hereby incorporated by reference in their entirety.

FIELD OF THE INVENTION

The present invention relates to methods and apparatus for measurement of changes in concentration of analytes of interest to detect the onset or early formation of potentially hazardous solids, in particular clathrates, such as gas hydrates. The methods and apparatus have particular applicability to the fields of petroleum and production engineering, gas production and gas processing, glycol regeneration, and flow assurance, for example in predicting and preventing hydrate formation.

BACKGROUND TO THE INVENTION

The past decade has witnessed dramatic changes in the oil and gas industry with the advent of deep-water exploration and production. Deep water exploration and production favours the formation of solid ice-like materials known as gas hydrates or clathrates. Clathrates are formed when polar molecules such as Water ($H_2O$) align through hydrogen bonding effects under the conditions of high pressure and (often low) temperatures typical of such deepwater locations to form hollow cage like structures that can trap and hold Carbon Dioxide ($CO_2$), Methane ($CH_4$) or other gases. These solid materials remain until they are subject to a change in their formation conditions (e.g. lower pressure or a higher temperature) that causes them to dissociate and release the trapped gases back to the surrounding atmosphere. There are several types of hydrate structure e.g. sI and sII that can form depending on the conditions of temperature, pressure and hydrocarbons present. It is known that sI hydrates form with lower molecular weight hydrocarbons such as Methane ($CH_4$), and that sII hydrates form preferentially with the presence of heavier hydrocarbons such as Propane ($C_3H_8$) or n-Butane/Iso-Butane ($C_4H_{10}$) making deepwater exploration where these are prevalent in the production streams potentially even more hazardous.

One of the major challenges within deepwater field development is to ensure unimpeded flow of hydrocarbons to the host platform or processing facilities; the early detection of the formation and managing the remediation of solids such as hydrate, wax, asphaltene and scale is key to the viability of developing deepwater prospects.

One of the problems other than blockage is the movement of the hydrate plugs in the pipeline at high velocity, which can cause rupture in the pipeline. Any blockage in an oil/gas pipeline due to hydrate is a serious threat to capital equipment and personnel safety. A number of strategies exist to inhibit or stop hydrate formation within transfer line or process facilities and one traditional approach is to remove or change one of the elements that favours hydrate formation such as temperature or pressure.

Examples of such strategies include thermal insulation or the external heating of transfer lines, water removal from natural gas using glycol dehydration systems, lowering operating pressure (mainly for removing blockage) or chemical approaches such as adding inhibitor materials to the system. Although often effective in reducing the formation of solids or treating the problem after the event, they increase OPEX or CAPEX. Despite the above prevention techniques, hydrates could form due to changes in the system conditions, inhibitor injection pump malfunction, error in calculating the amount of inhibitor required, etc. Currently there is no reliable technique in predicting the early formation of the solid hydrates themselves.

In support of these strategies, attempts have been made to detect early hydrate formation and a conference paper published by Tohidi et al. (SPE94340, EAGE Conference, Madrid, Spain, June 2005) describes a method for the early detection of hydrates based on measuring the dielectrical properties of reservoir fluids. The technique proposed by Tohidi et al. detects hydrate history by measuring the dielectric constant (permittivity) of aqueous samples. This method shows a high sensitivity to both chemical and physical contaminations of the sampling fluids that includes the presence of "micro bubbles" and other chemical additives; this can lead to false positive results that may affect its feasibility and reliability, which possibly hinders it for online application.

An alternative approach to measuring electrical properties was proposed by Tohidi et al. and is revealed in patent application, WO2006/054076. The method is based on identification of water memory by freezing point measurements. One drawback of this method is that freezing point measurements have a highly stochastic nature requiring a certain number of measurements to achieve the desired reliability/probability for hydrate early warning. Moreover, this freezing-point-based hydrate memory could be easily weakened even fully destroyed by the presence of certain hydrate inhibition additives.

There is no method or apparatus available for detecting either the onset or the early formation of hydrates in practice that could be used to inform the existing hydrate reduction strategies briefly outlined above—such a system would potentially reduce the need for high CAPEX heating/insulation, minimise the energy input to the heating systems, reduce inhibitor chemical usage and increase the safety of the personnel and capital equipment in deepwater exploration & production.

SUMMARY OF THE INVENTION

The present invention provides a method of detecting clathrate formation, in particular hydrate formation, the method comprising:
  monitoring a gas phase of interest, wherein the gas phase is a mixture of gases comprising at least one clathrate (e.g. hydrate) forming gas and the monitoring includes determining the concentration of at least one component of the mixture of gases; or determining a ratio of concentration between two components of the mixture, at least one of which is the said clathrate (e.g. hydrate) forming gas; and
  detecting a change in the determined concentration or in the determined ratio of concentration, relative to an earlier determination or relative to a pre-established base level concentration or base level range of concentration.

The monitoring of the gas phase may be continuous. For example continuous, typically automatic, sampling of a gas phase. Continuous monitoring may be by measurement at regular intervals (e.g. with an arrangement that takes samples at regular intervals and directs them into the analytical instrument) or even by means of constant analysis of the gas phase, for example by continuously measuring the gas phase by means of a suitable analytical instrument such as a Gas Properties Transmitter as discussed hereafter. Alternatively sampling may be intermittent with samples taken as thought necessary, for instance if a process upset has occurred and there is special concern that hydrates may be formed.

The following discussion of the invention is described in terms of hydrate formation. It will be appreciated that the formation of other clathrate materials may be detected in the same fashion, where a liquid other than water together with clathrate forming gases can form a clathrate structure.

The gas phase may be for example a gas phase associated with a hydrocarbon production stream from a gas and/or oil production well or collection of wells. In general a production stream will include three phases, gas/oil/water leading to the potential for hydrate formation. The gases present will typically include hydrate forming hydrocarbons (methane, propane, butanes etc) as well as e.g. carbon dioxide and nitrogen.

The gas phase monitored may be the naturally occurring gas phase in the production stream or may be a gas phase evolved from the aqueous phase or dissolved in the aqueous phase or even a gas phase evolved from or dissolved in the oil stream. As discussed below and with reference to specific embodiments the three phases are normally separated for processing/use of the gas and oil in a separator unit that can provide a convenient location for monitoring gases of one or more of the phases. Whilst gases dissolved in an aqueous phase or an oil phase may be conveniently monitored by causing the gases to evolve from the liquid phase e.g. by reducing pressure and/or by heating; it will be appreciated that dissolved gases in a liquid phase may be analysed directly, for example by hplc techniques. In general when sampling a hydrocarbon production stream process according to the methods described herein sampling points may be located at any location where an early indication of hydrate formation is useful. For example at a wellhead or a slug-catcher.

A change in a concentration or in a ratio of concentration may be observed by an operative who obtains the results of monitoring and makes calculations to check for a change in a value (concentration or concentration ratio) as appropriate. Advantageously a change is detected automatically and the result provided to an operative. For example the results of monitoring are compared with previous results or a base line level in a computer associated with the monitoring equipment. An alarm indication may be provided to alert an operative to a change, typically when a change is more than a predetermined minimum value.

Advantageously, especially where a hydrocarbon production stream is being monitored a ratio of concentration is measured, typically a ratio of concentration between two hydrate forming gases as discussed hereafter. Alternatively the ratio of concentrations between one hydrate forming component and another non hydrate forming component may be measured. This method can be notably sensitive especially when monitoring a gas evolved from or dissolved in an aqueous phase.

Most hydrocarbon systems have propane and butanes in varying amounts, promoting sII hydrate formation. Other gases such as hydrogen sulphide (H2S) also have a high affinity towards hydrate formation. As sII hydrates form they preferentially trap higher molecular weight hydrocarbons in their structures. This results in a reduction in the concentration of such compounds in the gas phase. On the other hand, the dissociation of hydrates (due to an increase in the system temperature and/or a reduction in the system pressure in their path to the production unit) results in a temporary increase in the concentration of these heavier compounds in the aqueous phase. Monitoring can be carried out on the gas content in or evolved from that aqueous phase. Using this behaviour we have found that we can detect whether hydrates are forming by directly measuring the changes in the composition or the ratio of the concentration of light (low molecular weight): heavy (high molecular weight) hydrate forming components present in the gas phase and/or the gas phase released from the produced water phase (i.e., the composition of gas present in the aqueous phase), as hydrates form, deep underwater or in transport lines. This technique can be used for detecting early signs of hydrate formation and as an early warning system against blockage due to hydrate formation.

Very lean gaseous systems (rich in methane and low in higher molecular weight hydrocarbons) form sI hydrates and a similar approach can be used for detecting initial signs of hydrate formation in such systems.

A further advantage of this method is that by knowing the speed of travel of the 2 respective gas and aqueous phases in the pipe or transfer line and the time lag between them arriving at a suitable detector it is possible to estimate the distance of the hydrate formation/blockage point from the detector.

The present invention therefore provides a method for detecting the early formation of hydrates, the method involving:

Analysing a gas phase of interest to establish a "Base level" concentration profile for each component present and/or ratios of different components and where appropriate establishing upper and lower limits for each component at the "Base level"

Continuously or intermittently monitoring the concentrations of the components present and/or ratios of different components in the gas phase of interest Recording the concentrations of each of the components present and/or ratios of different components in the gas phase of interest ("Measured level")

Comparing the "Measured level" vs. the "Base level" concentration profile and/or ratios of different components data Reporting any changes in the "Measured level" vs "Base Level" concentration profile and/or ratios of different components data Deciding on the significance of any change with respect to the probability of hydrate formation and Providing an automated "warning indicator" or similar notification to an agent that hydrates are forming enabling appropriate action to be taken The hydrate former can be any organic or inorganic molecule capable of being trapped within a hydrate structure as it forms or being released from a hydrate structure as it dissociates.

The gas phase of interest contains at least 2 different components; at least 1 of these is a hydrate former.

The gas phase of interest is typically a mixture of more than 2 components; at least 1 of these is a hydrate former.

The gas phase of interest ideally contains a mixture of hydrate former molecules of between 1 and "n" hydrate formers present in a range of concentrations; n is a multiplier with a value greater than zero (a whole number).

The gas phase of interest may be evolved from the dissociation of a hydrate material or released from an aqueous phase upon depressurisation; the hydrate material may be of any type.

The gas phase of interest may additionally contain one or more of Nitrogen ($N_2$), Carbon Dioxide ($CO_2$), Ammonia ($NH_3$), Water ($H_2O$), Carbon Monoxide (CO), Hydrogen Sulphide ($H_2S$), Hydrogen ($H_2$), Oxygen ($O_2$) or other gases.

The hydrate former molecules preferably contain Carbon (C) and Hydrogen ($H_2$) and may be saturated, unsaturated or cyclic in nature; examples of saturated hydrate former molecules of this type include Methane ($CH_4$), Ethane ($C_2H_6$), Propane ($C_3H_8$), n-Butane and Iso-Butane ($C_4H_{10}$), Pentane isomers ($C_6H_{12}$) etc. with a general molecular formula, $C_nH_{2n+2}$, where C is Carbon, H is Hydrogen and n is a multiplier with a value greater than zero (a whole number).

The hydrate former may be free of Carbon (C); examples of such formers include Ammonia ($NH_3$), Hydrogen ($H_2$) or Hydrogen Sulphide ($H_2S$).

The hydrate former may be free of Hydrogen (H); an example of such a material is Carbon Dioxide, $CO_2$.

The hydrate former may be from the family of Noble gases; an example gas of this type is Argon, Ar.

Optionally the methods of detecting formation of clathrates such hydrates described herein may include the step of adding of one or more gases that form clathrates or hydrates to a gas phase being monitored. These tracer compounds may be, for example, the various hydrate forming compounds discussed above, where they are not already present or present in sufficient quantity to permit operation of the method with the analytical equipment being employed. Alternatively or additionally other compounds such as $SF_6$ or fluorocarbons such as R152a (1,1-difluoroethane) that are not normally found in oil production streams may be employed as tracer compounds. Tracer compounds can also include the odorants such as dimethyl sulphide and t-butyl mercaptan that are normally added to gas supply systems to allow easy detection of leaks. Certain compounds (e.g., $H_2S$) can be detected and monitored at very low, for example ppm or ppb levels. Thus they can be employed economically as tracers in the method. The tracer compounds may be hydrate formers or non hydrate forming.

The concentration or change in concentration of the hydrate former(s) in the gas phase of interest is determined and recorded using a suitably accurate analytical technique capable of distinguishing the components of a mixture including at least 1 hydrate former species from each other. Gas chromatography is one such suitably robust technique offering repeatability of results and high accuracy that can be used in-line (with a suitable sampling loop), at-line or off-line in a laboratory situation. An alternative instrument is a "Gas Properties Transmitter (GasPT)" that is commonly used in gas transportation & processing technology for measuring various properties of gas mixtures. A GasPT instrument can provide a sufficiently accurate estimate of gas component concentrations for the purposes of the present invention, by carrying out measurements of various physical properties of a gas mixture. These measurements of physical properties such as thermal conductivity and speed of sound are used to infer gas phase concentrations assuming four components (methane, propane, carbon dioxide and nitrogen). As illustrated hereafter by an example, the concentrations determined by such an approach can be used to indicate hydrate formation. Other instruments can be used in the same way to take measurements of physical properties of a gas phase (such as speed of sound, thermal properties, electrical properties) to determine concentrations by similar estimating techniques, where a gas phase composition is inferred.

The concentrations of the hydrate formers in the gas phase of interest are optionally measured and recorded on a continuous or intermittent basis to establish a "base level" or "steady state condition" over a period of time. Establishing a "base level" is preferred as it will show natural variation in gas composition with time (background noise) but is not essential as sudden changes in concentration between subsequent measurements can be indicative of hydrate formation. It is also possible to predict expected (base level) concentration and then measure actual concentrations for comparison against the predicted level. For example the composition of gas released from a separator unit in an oilfield production stream can be predicted on the basis of the feed composition and the pressure and temperature conditions. Gas released from an aqueous phase produced at the separator will also have a predictable composition. These predictions can provide a baseline level.

During operation, the concentration profiles of the hydrate formers are measured and recorded continuously or intermittently and compared to those of the "base level" or a recent measurement and any changes in concentration profile noted.

A change in the concentration and/or the ratio of the measured hydrate former concentration to each other or a non hydrate former in relation to the baseline or steady state condition is indicative of the onset of hydrate formation, e.g. for a mixture of Hydrocarbon formers/components:

A decrease in the Low carbon number hydrate formers e.g. Methane ($CH_4$) in the gas phase is indicative that Type sl hydrate is preferentially forming A decrease in higher carbon number hydrate formers (e.g. Propane & Butanes) in the gas phase is indicative that type sII hydrates are forming.

The information on the change in ratio of hydrate formers to each other can inform or provide a warning to an agent that hydrates are forming and that remedial action is required.

The change in ratio can be sudden or gradual; sudden changes in concentration could be indicative of potentially catastrophic equipment failures such as thermal insulation loss, heater failure or of process issues such as flow rate changes, inhibitor injection pump dosing problems etc. on a transfer line causing rapid hydrate formation.

The method for detecting hydrate formation can be implemented in different approaches according to the quantity of hydrate that forms in relation to the gas flow rate:

(1) If more than 5 Barrels of water is (could be) converted into gas hydrates per 1 MMSCF (MMSCF or Million Standard Cubic Feet is a volume unit in the petroleum industry) of gas transported (also assuming the background noise is not too high), direct analysis of the composition of the gas phase can be applied to identify early hydrate formation, following the procedures described previously.

(2) If less than 5 Barrels of water is (could be) converted into gas hydrates per 1 MMSCF of gas transported, the gas released from aqueous phase after hydrate dissociation can be analysed. This option can be used when the change in the gas phase composition is not sufficiently large for ready detection e.g. due to background noise.

Option 2, above, is also applicable at higher hydrate formation rates. However either approach may be useful in some circumstances irrespective of amount of hydrate being formed provided suitably sensitive measurement techniques are employed. Advantageously both the options above are employed.

The methods described herein may be carried out manually, with an operator carrying out the monitoring using suitable analytical equipment and then acting on the results obtained, or partially automatically, or fully automatically. For example the analytical equipment may be programmed to calculate when a change in concentration, from a baseline level or from an earlier measurement exceeds a predetermined level and signal an alarm. Alternatively a fully automatic system may send an alarm signal to a control system which takes a predetermined remedial action (process adjustment) or emergency action such as a shut down procedure.

The present invention provides an apparatus for carrying out a method of detecting clathrate formation, in particular hydrate formation, the apparatus comprising:

means for monitoring a gas phase of interest that comprises at least one clathrate forming (e.g. hydrate forming) gas, the monitoring including determining the concentration of at least one component of the mixture of gases; or determining a ratio of concentration between two components of the mixture, at least one of which is the said clathrate forming (e.g. hydrate forming) gas;

means for detecting a change in the determined concentration or in the determined ratio of concentration, relative to an earlier determination or relative to a pre-established base level concentration or base level range of concentration; and means for generating an alarm signal as a result of the detected change in the determined concentration or in the determined ratio of concentration.

Typically the apparatus includes: a sampling device (e.g. a valved port in a pipe or vessel), to obtain from a process stream a gas sample and/or a water sample containing dissolved gases; optionally an apparatus for reducing pressure of a water sample to release dissolved gases into a gas phase; analytical apparatus (e.g. a gas chromatograph or a GasPT device) to determine gas concentration or ratio of concentration; and a processor e. g. a PC or a processor within the analytical apparatus, to carry out calculations of concentration or concentration ratio and compare with earlier results or a base level value or range and to generate an alarm signal. The alarm signal can be output to a visual display (e.g. a screen or a light) and/or an audible alarm sounder (e.g. buzzer or siren).

The present invention provides a system for controlling a hydrocarbon production stream process, the system comprising:

means for monitoring a gas phase from the process to detect hydrate formation in the hydrocarbon production stream in accordance with the methods described herein; and a control system operable in response to an alarm signal generated as a result of the monitoring to carry out adjustment of process conditions and/or shut down procedures. The adjustment of process conditions can include a change in injection rate of hydrate inhibitors Typically the system will also provide an alarm to a process operator, for example to allow manual override.

The present invention provides a method for estimating the position of hydrate formation in a pipeline carrying both a gas phase and an aqueous phase, wherein the gas phase is a mixture of gases including at least one hydrate forming gas, the method comprising:

determining the velocities of the gas phase and the aqueous phase in the pipeline;

monitoring at a sample position, both the gas phase and the aqueous phase, to detect formation of hydrate by the methods described herein; and estimating the distance of the hydrate formation position from the sample point based on the time difference between detection of an indication of hydrate formation in the gas phase and in the aqueous phase and the determined velocities of the respective phases in the pipeline.

The velocities of the gas phase and of the aqueous phase can be determined on the basis of the flow rates of the respective phase, pipe dimensions and geometry, physical properties of the phases

BRIEF DESCRIPTION OF THE DRAWINGS

Various aspects of the invention will now be described by way of example only and with reference to the following drawings, of which.

DESCRIPTION OF SOME PREFERRED EMBODIMENTS AND EXPERIMENTAL RESULTS

Figure 1:
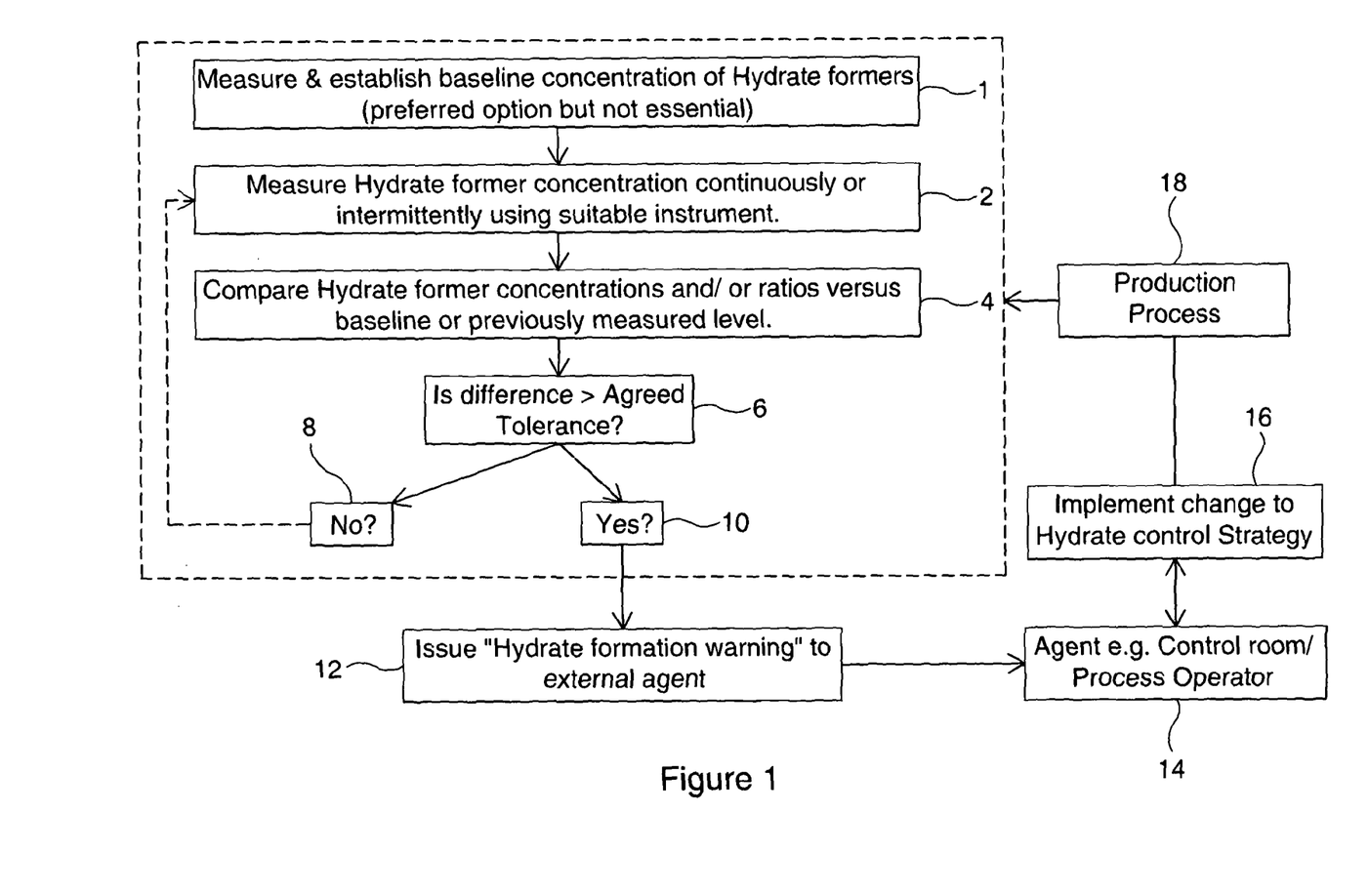
FIG. 1 shows a simplified schematic diagram of a method of detecting hydrate formation.

FIG. 1 represents a simplified schematic diagram of an embodiment of the method explaining the key stages. A model production process is shown in which a baseline level of concentration or ratios of concentrations has been established (preferred option but not essential), monitoring of the process using a suitable analytical instrument is occurring on a continuous or intermittent basis and any significant difference in Hydrate former is reported to an external agent (e.g. a control room or process operator) who, using the information, then adjusts the process/hydrate mitigation strategy to minimise/stop hydrate formation. The figure shows the process as a block diagram as follows: Firstly 1 a series of measurements is taken of the gas phase being monitored to establish a baseline level for the concentration or concentration ratio of selected gas or gases. A baseline may also be established by prediction based on an understanding of the input to the production process and the operating conditions. The baseline level may be obtained as a discrete value or a range of typical values dependent on the consistency of the gas mixture being examined. Then 2 the concentration or concentration ratio is monitored by continuous or intermittent monitoring by means of a suitable analytical technique. The results of the monitoring in 2 are then compared 4 with the baseline level or earlier monitoring results to determine 6 if any difference in results has been found. Typically a difference is regarded as significant only when exceeding a pre-determined tolerance level. The monitoring and checking for differences may be carried out automatically e.g. by an analytical instrument including or coupled to a computer. If no significant difference in the result is found 8 then the process of monitoring 2 is continued as desired. If a significant difference is found 10 then a warning signal 12 is generated and issued to an external agent such as a control room or process operator 14, who can then implement corrective or emergency action 16 such as an adjustment of process conditions or a shut down of the production process 18. The warning signal 12 may be part of a fully automatic system (e.g. computer control system) that acts as external agent 14 to carry out the desired actions 16.

Figure 2:
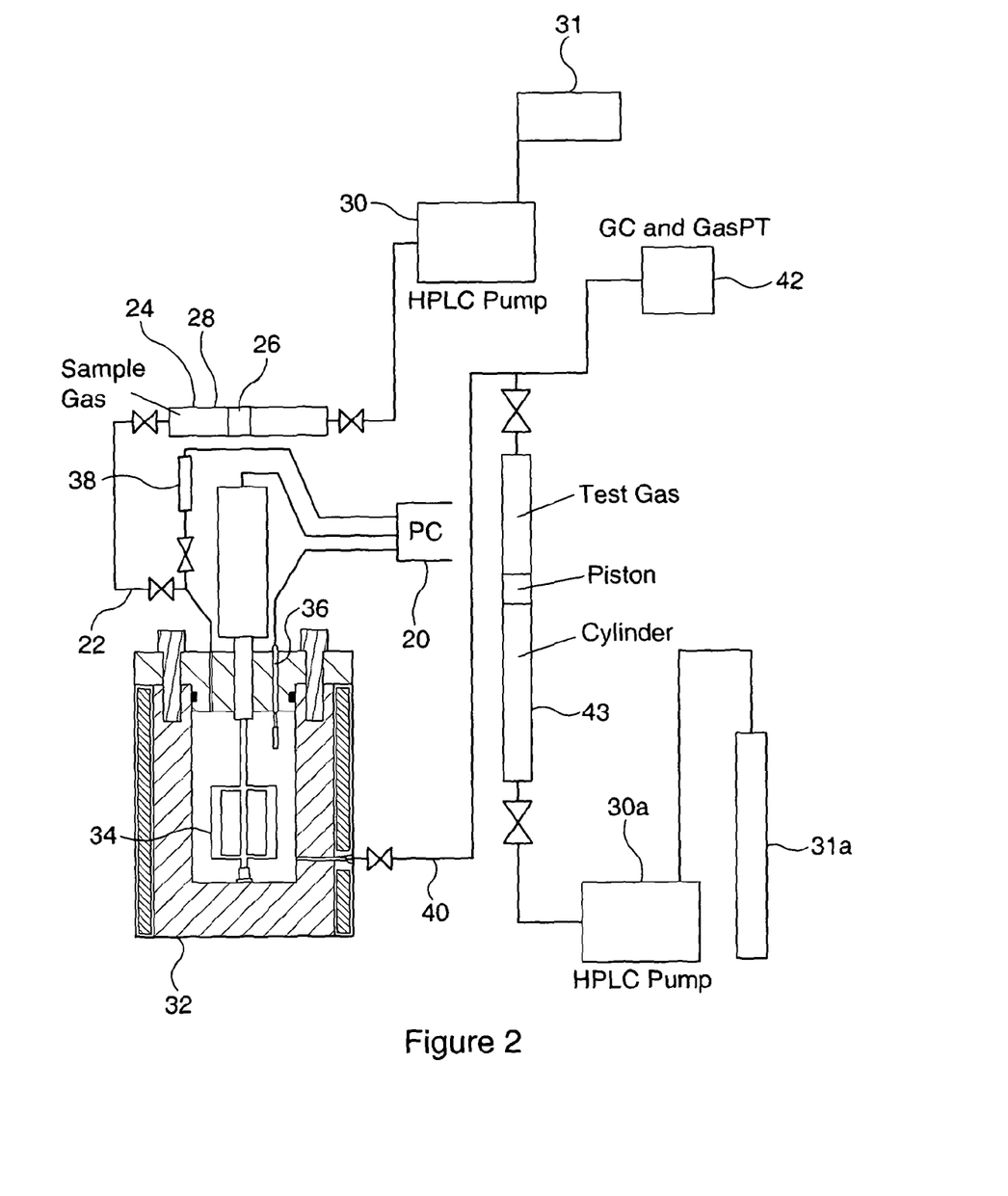
FIG. 2 shows a schematic diagram of an apparatus for testing hydrate formation.

FIG. 2 represents an apparatus of a design suitable to test gas hydrate former mixtures under "Hydrate forming" conditions of temperature and pressure. Controlled by a suitable PC 20, the system comprises a controllable gas inlet 22 from a sample chamber 24 that includes a piston 26 for pressurising a gas sample 28 by means of a pump 30, supplied with water from a reservoir 31, to a temperature controlled high pressure autoclave chamber 32 fitted with a stirrer 34, temperature and pressure transducers 36, a pressure transducer 38 and a controllable inlet/outlet 40 to a pressure adjusting chamber (piston chamber) 43 in the form of a piston in cylinder arrangement controlled by another pump 30a and associated water supply 31a in this example. A suitable detector 42 such as a Gas Chromatograph or GasPT instrument is available for testing gases from the pressure adjusting chamber 43. The detector 42 can also be connected to sample chamber 24 for measurement of its contents. It will be obvious that the controllable outlet 40 could be re-positioned to collect either a sample of the aqueous phase or the gas phase. The system is designed for safe operation under high pressure conditions. The operation of the apparatus is described under the heading "Example 2" below.

Figure 3:
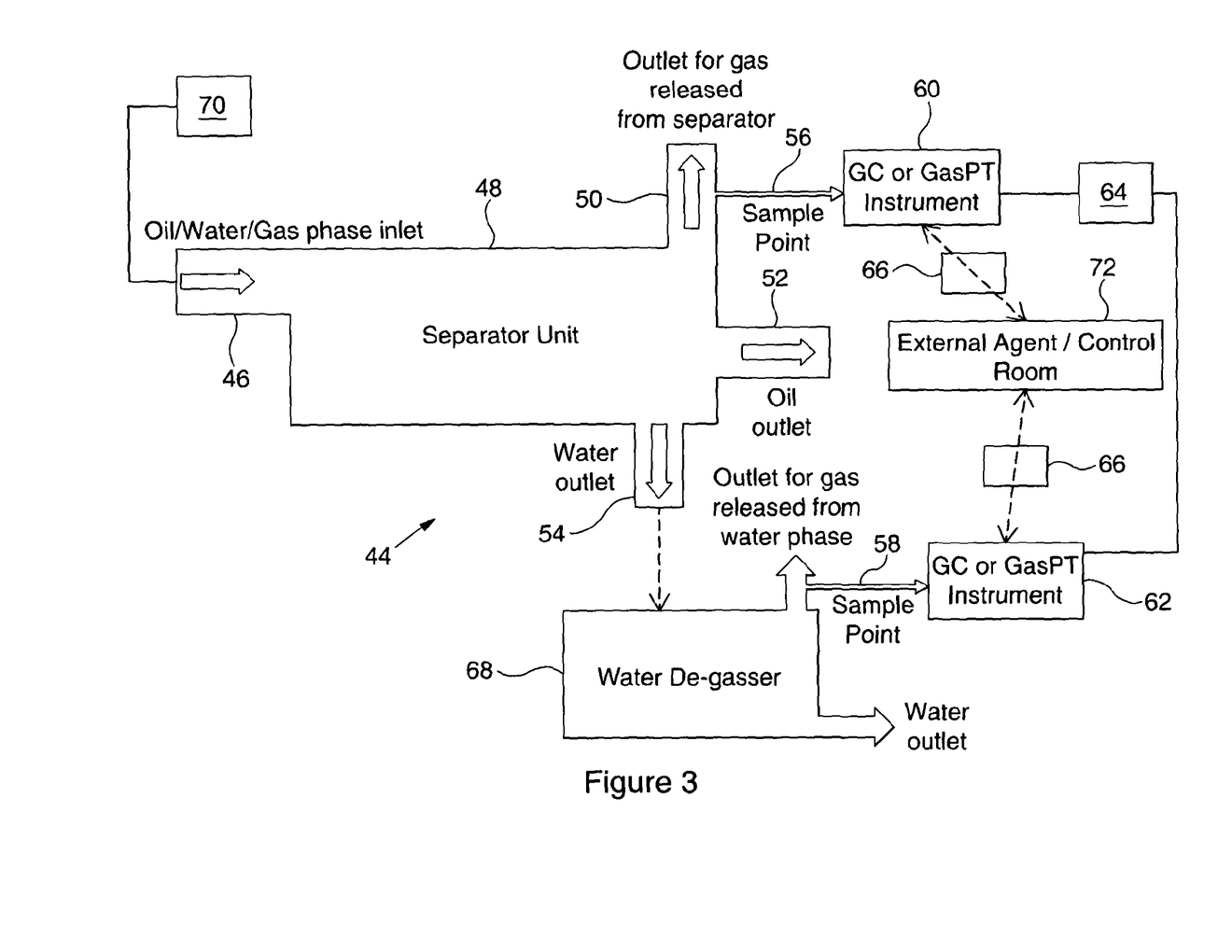
FIG. 3 shows schematically a simplified Gas/Oil/Water separator system.

FIG. 3 represents a simplified Gas/Oil/Water separator system 44 (or slugcatcher) that could be used in an oil and gas production process comprising of a high pressure delivery line 46 containing a mixture of gas and liquid phases, a lower pressure separator stage 48 where the phases are separated into Gas 50, Oil 52 and Water 54 streams respectively, suitable sampling points 56,58 for collecting samples of interest, apparatus 60,62 for measuring, recording and comparing the concentrations of hydrate formers in the collected samples, a power supply 64 and at least one communication device 66 for data transference. The separated water phase can pass to a subsequent "de-gassing unit" 68 to dissociate any hydrates present or recover dissolved gases.

EXAMPLE 1

Prediction of Hydrate Formation by Analysis of the Gases Present in a Gas Phase

In oil & gas processing the oil/gas/water phases are often under high pressure and to facilitate further processing these are first separated from each other using a 3-phase separator crudely represented (a schematic figure) by the design of FIG. 3. This involves depressurisation and separation into 3 separate streams (Oil 52, Gas 50 & Water 54) that can be analysed using suitable sample points 56,58.

It is known that hydrates form under certain conditions of temperature and pressure in the presence of suitable formers and that the presence of hydrates or the differential composition of a gas mixture can affect the speed of sound (SoS) as it travels through a medium. To demonstrate the effect of hydrate formation on gas composition and the speed of sound, a series of experiments was undertaken using a known gas mixture where different amounts of water were converted into hydrates (from 1 Barrel/MMSCF to 100 Barrel/MMSCF) in the presence of the gas mixture (Note: MMSCF, million standard cubic feet is a measure of gas volume transported). The results are presented graphically in FIG. 4, which shows the amount of water (expected to be converted to hydrate) expressed as Barrels/MMSCF. The left hand columns show the speed of sound (SoS) where hydrate formation has been induced and the right hand columns where hydrate formation has not occurred.

Figure 4:
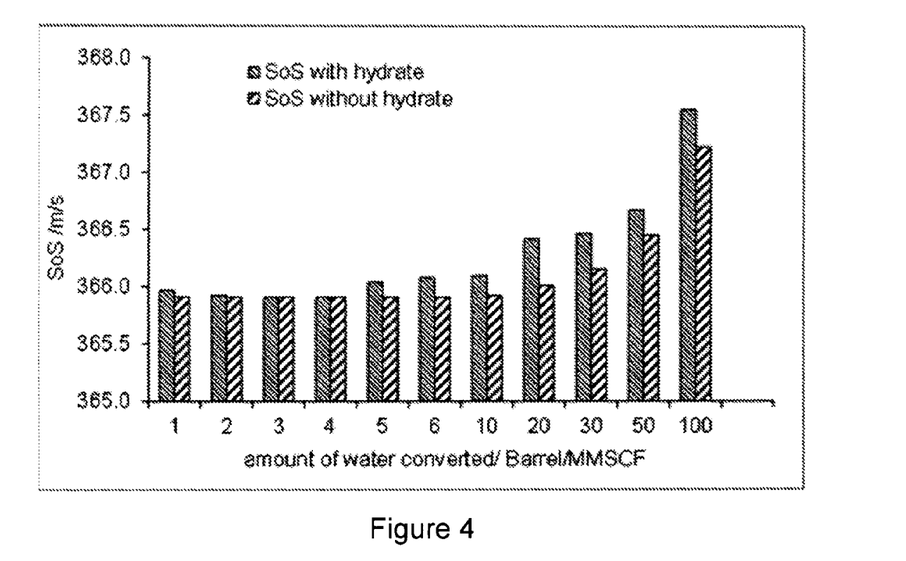
FIG. 4 shows graphically speed of sound (SoS) change for different amounts of hydrate formation.

It should be noted that the amount of hydrates formed were increased in these experiments by increasing the system pressure, hence an increase in the SoS in the right hand columns (without hydrate formation). In real conditions, the system pressure and temperature is normally constant, hence the baseline SoS should remain constant. Therefore, any change in speed of sound can be attributed to change in gas composition, hence hydrate formation.

The above graph shows that there is a measureable change in speed of sound from the region beyond where ≥5 Barrel/MMSCF of water is converted into hydrate. As shown in the graph, an increase in the amount of water converted into hydrate results in an increase in the change in the speed of sound.

To confirm the results shown in the above graph and to note any respective changes in the gas composition as the hydrates are formed; a commercial instrument known as a GasPT (available from manufacturers such as Germanischer Lloyd Group of Hamburg, Germany) was used to measure the gas composition. GasPT is a familiar instrument within gas transport or processing industry and gives an output based on physical properties of the gas mixture to calculate equivalent concentrations of Methane ($CH_4$), Propane ($C_3H_8$) and other gases of interest present (i.e., $N_2$ and $CO_2$). A gas chromatograph instrument (GC) could also be used to measure the gas composition.

Table 1 (below) shows the results of the measurements by the GasPT instrument at different water contents ranging from 1 Barrel/MMSCF to 50 Barrel/MMSCF. In addition to the increasing speed of sound, the results confirm that the ratio of Propane to Methane is decreasing as the amount of water converted to hydrate increases. At ~5 Barrel/MMSCF this change is detectable, using this instrument, in a range outwith that of the background noise inherent within the system. Therefore in this example the ratio of concentrations technique can quickly detect hydrate formation in a system where about 5 or more Barrels of water might be converted to hydrate per MMSCF of gas.

TABLE 1

Results of the measurements by the GasPT instrument

| Barrels of water | SoS | Equiv. $CH_4$ | Equiv. $C_3H_8$ | Equiv. $CO_2$ | Equiv. $N_2$ | $C_3/C_1$% |
|---|---|---|---|---|---|---|
| NG (blank) | 417.854 | 92.445 | 4.759 | 1.864 | 0.927 | 5.148 |
| 1 | 417.934 | 92.449 | 4.757 | 1.865 | 0.930 | 5.145 |
| 5 | 418.058 | 92.368 | 4.608 | 1.856 | 1.168 | <u>4.989</u> |
| 10 | 417.937 | 92.348 | 4.574 | 1.882 | 1.195 | 4.952 |
| 30 | 418.562 | 92.841 | 4.444 | 1.814 | 0.900 | 4.787 |
| 50 | 419.619 | 92.882 | 4.324 | 1.785 | 1.008 | 4.656 |

Thus the changes in the composition of the gas phase as hydrate forms can be used as the basis of a method to predict the onset of hydrate formation allowing operators to take pre-emptive action to change the process conditions; this is especially useful in industrial oil/gas processing or transportation situations where hydrate formation is often detected only "after the event" i.e. once a pipe has blocked and requires costly remedial action. The method could be introduced to industrial practice in the process of FIG. 3 by sampling the gases being released from the gas/liquid phase separator 48 using a suitable instrument (GC or GasPT) and comparing and reporting the results.

EXAMPLE 2

Prediction of Hydrate Formation by Analysis of the Gases Evolved from an Aqueous Phase For the cases where either not much water is present in transfer lines or there is not much water converted into hydrates (e.g. ≤5 Barrels per MMSCF) direct measurement of the changes in composition of the gas phase is sometimes impractical and an indirect method can be used where the gases evolved from hydrate dissociation or gases released from the aqueous phase are measured.

FIG. 2 shows an experimental high pressure autoclave apparatus suitable for making hydrates and testing their properties under controlled conditions of temperature and pressure.

A baseline hydrate former level is measured by charging a volume of water (1000 cc) to the autoclave 32 chamber (2400 cc internal volume) and pressurising this with natural gas (e.g., a mixture of Methane, Ethane, Propane and Butanes) through the inlet valve to 1500 psia and maintaining the temperature at 19.5° C. (with stirring) until equilibrium had been reached (~10 minutes).

Once equilibrium is reached, the pressure in the autoclave 32 was reduced to 300 psia prior to transferring a sample of the aqueous phase to the piston vessel 43 of FIG. 2. The valve was closed and the pressure within the piston decreased sufficiently to allow any dissolved gases (hydrate dissociation products) to evolve. In this case, the conditions of less than 800 psia and 19.5° C. were chosen for the piston vessel as they are representative of a separator (degasser) process within an Oil & Gas production platform. The test gas was then analysed by the GC/GasPT instrument 42 and the concentrations of Methane, Ethane, Propane and Butanes recorded as a baseline level.

To represent hydrate forming within a pipeline, a second experiment was conducted on the same natural gas sample by increasing the pressure and reducing the temperature to "Hydrate forming conditions" before allowing the mixture to reach equilibrium with stirring. The pressure was maintained at separator conditions (i.e. 300 psia) and the hydrate dissociated by changing the temperature of the apparatus to 3° C. outside that of the phase boundary of the hydrate. An aqueous sample was transferred to the piston vessel 43 at about 300 psi and measuring the composition of the gases using the GC/GasPT instrument 42.

Figure 5:
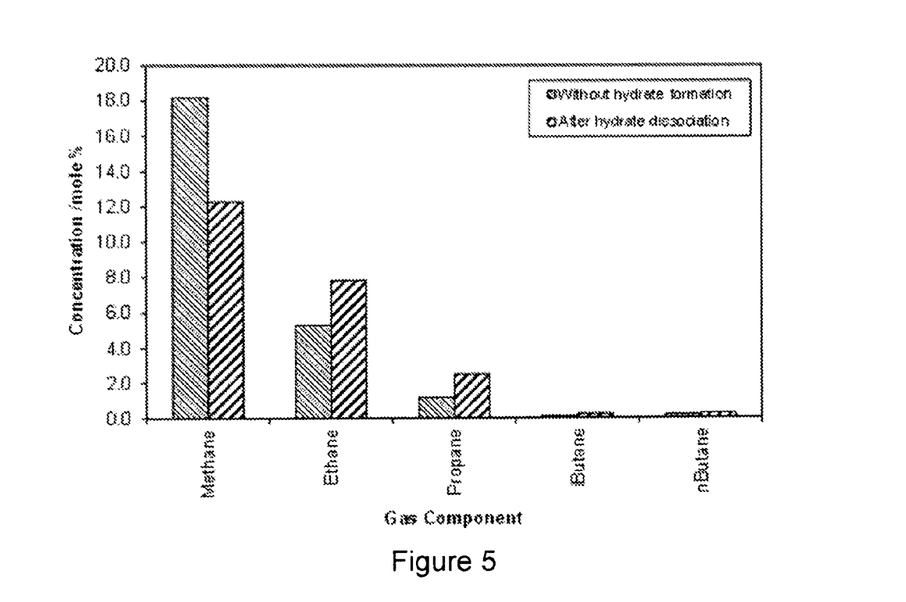
FIG. 5 shows graphically concentrations of different components of gases before and after Hydrate formation.

The composition (i.e. concentration of different components) of the gases before and after Hydrate formation are shown in FIG. 5 (those without Hydrate formation are represented by the left hand columns).

(The columns showing methane concentration are not to scale in this graph to allow easier viewing of the change in concentrations of the higher molecular weight hydrocarbons. The actual methane concentrations it the test sample can be obtained from the graph by adding 75 to the indicated value. Thus the methane concentration in the sample without hydrate formation (left hand column) was 93%.)

The concentrations of the other components in the mixture are to scale. It can be seen that the concentration of Methane has decreased and the concentrations of Ethane, Propane (and to a lesser extent) the Butanes in the evolved gas phase have increased significantly due to the formation and subsequent dissociation of the hydrates.

EXAMPLE 3

Prediction of Hydrate Formation by Analysis of the Gas Evolved from an Oil, Gas & Water Mixture Using the apparatus of FIG. 2 a second experiment representing an oil production process where a mixture of oil, gas and water are charged to a separator stage was devised. In this case 300 cc of hydrocarbon oil and 1000 cc of water were charged into the Autoclave 32, A baseline test was first performed as before by pressurising the apparatus to 1500 psia with natural gas, equilibrating and then transferring a water sample to the piston chamber 43 before lowering the pressure in the piston chamber 43 to 300 psia and analysing and recording the evolved gas concentrations using the GC/GasPT instrument.

The temperature was then decreased to "Hydrate forming conditions" and allowed to equilibrate before increasing the temperature to 3° C. outside the hydrate phase boundary. An aqueous sample was transferred to the piston vessel 43 at about 300 psia and measuring the composition of the gas released using the GC/GasPT instrument.

Figure 6:
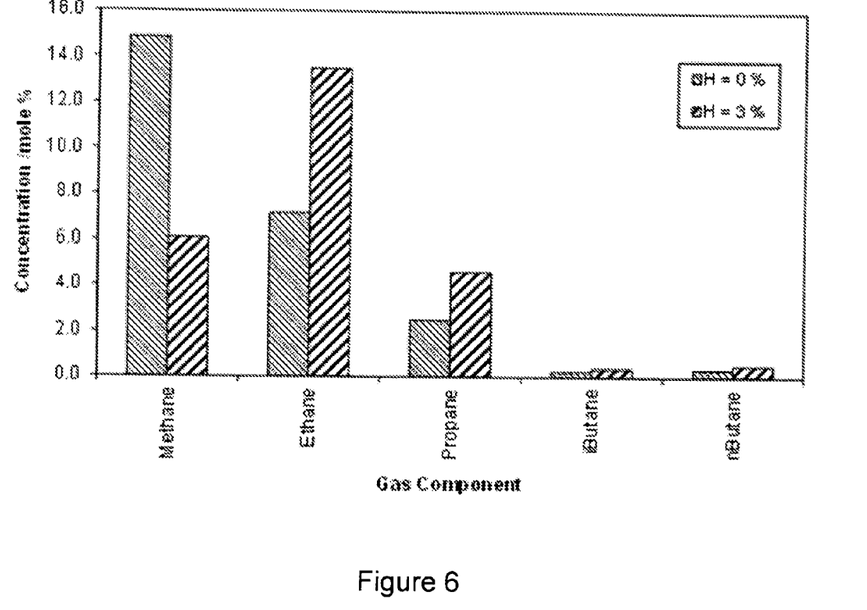
FIG. 6 shows graphically concentrations of various components before and after Hydrate formation.

The concentrations of various components before and after Hydrate formation are shown in FIG. 6 (those without hydrates are indicated by left hand columns). (The columns showing methane concentration are not to scale in this graph to allow easier viewing of the change in concentrations of the higher molecular weight hydrocarbons. The actual methane concentrations it the test sample can be obtained from the graph by adding 75 to the indicated value as for graph 2 above.)

When hydrates form there is a significant change in the concentrations of the heavier components in the evolved gas phase.

Thus direct measurement of the gases evolved from the aqueous phase in an oil/water/gas mixture and comparison to a steady state process or a baseline measurement provides an early indication whether the oil/gas/water mixture was subjected to a hydrate formation.

It will be obvious that the method proposed within the above 3 examples can be introduced to industrial practice to measure the change in concentration of hydrate formers present in a gas phase or the gases evolved from a water phase. With reference to FIG. 3, a pipeline/manifold 70 carrying a mixture of oil, gas and water under pressure from a reservoir is shown connected to a separator unit 48 within a process facility. Within the separator unit the pressure is lowered sufficiently that the gas phase can be collected and the oil/water passes through for further processing. An analytical instrument, a GC or GasPT, 60 or 62 or other suitable instrument is shown connected to a suitable sample collection point 56 or 58, the sampling point being in a position to collect either one of a sample of gas directly from the separator or a sample of gas evolved from the liquid/aqueous phase (depending on the volume of produced water) or both of them. The produced water phase may be subject to a depressurising procedure in a depressurising stage 68 to release gas retained within it. The collected gas sample is analysed and the concentrations and/or ratios of gases preferentially compared to a reference (baseline or a period of steady state operation). Any changes in concentration that could indicate the formation of hydrates are notified to an agent 72 such as a process operator or control room for remedial action. The communication may be by a communication device 66 such as a wireless or a wired linkage.

EXAMPLE 4

Estimation of the Hydrate Blockage or Formation Position in a Transport Line Using the Described Method The gas and liquid phases in a pipeline often travel at different speeds depending on their density and viscosity, pipeline hydrodynamics, etc and this will affect their time of arrival at a process plant—when combined with the information on the changes in the composition as hydrates begin to form, this can be used to approximate the hydrate formation point within the pipeline providing potentially a means of directing remedial action.

In a production process where there is a high hydrate conversion (≥5 barrels per MMSCF), it is possible to directly analyse the gas phase using the methods described in Example 1. As a typical example, we assume the speed of arrival in the separator 48 of FIG. 3 is 11 meter/second for the gas phase, and 1 meter/second for the liquid phase, in the transfer line. Assuming that the gas phase and the gas released from the aqueous phase are analysed continuously then the initial sign of hydrate formation will be detected first by the free gas phase analysis as gas moves much faster than the liquid phase. The change in the composition of the gas released from the aqueous phase will be detected later as the aqueous phase moves much slower. For example if there is a 10 minutes time difference in detecting the signs of hydrate formation from the two techniques, the point of hydrate formation can be estimated as:

Estimated distance=(Detection Time difference in seconds)×(gas velocity−aqueous phase velocity in m/second)

For the above case:

(10 min×60 sec/min)×(11−1)=6,000 m

So hydrates are forming at around 6 km away from the sampling point.

A skilled person will appreciate that variations of the disclosed arrangements are possible without departing from the invention. Accordingly the above description of specific embodiments are made by way of example only and not for the purposes of limitation. It will be clear to the skilled person that minor modifications may be made without significant changes to the operation described. For example the system shown in FIG. 3 may be fully automatic, with results of monitoring activating a suitable control system, resulting in automatic adjustment of process parameters or emergency shut down according to predetermined parameters.

The invention claimed is:

1. A method of detecting clathrate formation, the method comprising:
   monitoring a gas phase of interest, wherein the gas phase is a mixture of gases comprising at least one clathrate forming gas and the monitoring includes determining the concentration of at least one component of the mixture of gases; or determining a ratio of concentration between two components of the mixture, at least one of which is the said clathrate forming gas; and
   detecting a change in the determined concentration or in the determined ratio of concentration, relative to an earlier determination or relative to a pre-established base level concentration or base level range of concentration.

2. The method of claim 1 wherein the clathrate is a gas hydrate and the mixture of gases comprises at least one hydrate forming gas.

3. The method of claim 1 wherein the monitoring comprises sampling of the gas phase at regular intervals or constantly.

4. The method of claim 1 wherein the monitoring comprises sampling of the gas phase automatically.

5. The method of claim 2 wherein the gas phase monitored is associated with a hydrocarbon production stream.

6. The method of claim 5 wherein the gas phase monitored is selected from the group consisting of:
   a naturally occurring gas phase in the production stream; a gas phase evolved from the aqueous phase; a gas phase dissolved in an aqueous phase; a gas phase evolved from a hydrocarbon oil phase; and a gas phase dissolved in a hydrocarbon oil phase.

7. The method of claim 1 wherein the change in the determined concentration or in the determined ratio of concentration is detected automatically and the result provided to an operative.

8. The method of claim 1 wherein a ratio of concentration between two clathrate forming gases, or between one hydrate forming and one non-hydrate forming gas, is monitored.

9. The method of claim 1 wherein determination of concentrations or ratio of concentrations is carried out by means of gas chromatography or by use of a gas properties transmitter.

10. The method of claim 1 further comprising sending an alarm signal to a control system configured to take a predetermined remedial action or initiate a shut down procedure when a change in the determined concentration or in the determined ratio of concentration, exceeds a predetermined level.

11. The method of claim 1 further comprising the addition of at least one tracer compound for monitoring in the gas phase of interest.

12. An apparatus for detecting clathrate formation, the apparatus comprising:
   a gas chromatograph or a Gas properties transmitter apparatus for monitoring a gas phase mixture comprising at least one clathrate forming gas, the monitoring including determining the concentration of at least one component of the mixture of gases; or determining a ratio of concentration between two components of the mixture, at least one of which is the said clathrate forming gas;
   a processor or PC coupled to the gas chromatograph or the Gas properties transmitter apparatus configured for detecting a change in the determined concentration or in the determined ratio of concentration, relative to an earlier determination or relative to a pre-established base level concentration or base level range of concentration, and
   for generating an alarm signal as a result of the detected change in the determined concentration or in the determined ratio of concentration.

13. The apparatus of claim 12 wherein the clathrate is a gas hydrate and the gas phase mixture comprises at least one hydrate forming gas.

14. The apparatus of claim 12 further comprising a sampling device for obtaining samples from a process stream.

15. A system for controlling a hydrocarbon production stream process, the system comprising:
   an apparatus for detecting hydrate formation according to claim 13; and
   a control system operable to carry out adjustment of process conditions and/or shut down procedures in response to the alarm signal generated.

16. A method for estimating the position of hydrate formation in a pipeline carrying both a gas phase and an aqueous phase, wherein the gas phase is a mixture of gases including at least one hydrate forming gas, the method comprising:
   determining the velocities of the gas phase and the aqueous phase in the pipeline;
   monitoring at a sample position, both the gas phase and the aqueous phase, to detect formation of hydrate by the method of claim 1; and
   estimating the distance of the hydrate formation position from the sample point based on the time difference between detection of an indication of hydrate formation in the gas phase and in the aqueous phase and the determined velocities of the respective phases in the pipeline.

* * * * *